US011351127B2

(12) United States Patent
Hansen et al.

(10) Patent No.: US 11,351,127 B2
(45) Date of Patent: Jun. 7, 2022

(54) PHARMACEUTICAL COMPOSITION

(71) Applicant: Avexxin AS, Trondheim (NO)

(72) Inventors: Philip Hansen, Hosrsholm (DK);
Anders Ljungqvist, Trondheim (NO)

(73) Assignee: Avexxin AS, Trondheim (NO)

( * ) Notice: Subject to any disclaimer, the term of this patent is extended or adjusted under 35 U.S.C. 154(b) by 142 days.

(21) Appl. No.: 16/334,835

(22) PCT Filed: Sep. 21, 2017

(86) PCT No.: PCT/EP2017/073958
§ 371 (c)(1),
(2) Date: Mar. 20, 2019

(87) PCT Pub. No.: WO2018/055062
PCT Pub. Date: Mar. 29, 2018

(65) Prior Publication Data
US 2020/0261378 A1    Aug. 20, 2020

(30) Foreign Application Priority Data

Sep. 21, 2016  (GB) .................................... 1616093
May 24, 2017  (GB) .................................... 1708329

(51) Int. Cl.
*A61K 31/121*  (2006.01)
*A61P 19/02*  (2006.01)
*A61K 47/14*  (2017.01)
*A61K 47/26*  (2006.01)
*A61K 47/34*  (2017.01)

(52) U.S. Cl.
CPC ............ *A61K 31/121* (2013.01); *A61K 47/14* (2013.01); *A61K 47/26* (2013.01); *A61K 47/34* (2013.01); *A61P 19/02* (2018.01)

(58) Field of Classification Search
CPC ...... A61K 31/121; A61K 47/14; A61K 47/26; A61K 47/34; A61P 19/02
See application file for complete search history.

(56) References Cited

U.S. PATENT DOCUMENTS

| | | | |
|---|---|---|---|
| 4,649,215 A | 3/1987 | von Sprecher et al. | |
| 4,670,465 A | 6/1987 | Guzman et al. | |
| 6,255,496 B1 | 7/2001 | Banville et al. | |
| 6,688,468 B2 | 2/2004 | Waterman | |
| 7,101,875 B2 | 9/2006 | McKew et al. | |
| 7,667,039 B2 | 2/2010 | Garcia-Echeverria et al. | |
| 7,687,543 B2 | 3/2010 | Johansen et al. | |
| 8,524,776 B2 | 9/2013 | Johansen et al. | |
| 8,796,251 B2 | 8/2014 | Johansen et al. | |
| 8,865,768 B2 | 10/2014 | Johansen et al. | |
| 9,187,396 B2 | 11/2015 | Johansen et al. | |
| 9,375,409 B2 | 6/2016 | Johansen et al. | |
| 9,682,930 B2 | 6/2017 | Feuerherm et al. | |
| 10,085,952 B2 | 10/2018 | Johansen | |
| 10,085,953 B2 | 10/2018 | Johansen et al. | |
| 2005/0165116 A1 | 7/2005 | Johansen et al. | |
| 2005/0256141 A1 | 11/2005 | Nakagawa et al. | |
| 2005/0281755 A1 | 12/2005 | Zarif et al. | |
| 2005/0282792 A1 | 12/2005 | Andres | |
| 2006/0162240 A1 | 7/2006 | Filippini et al. | |
| 2008/0063607 A1 | 3/2008 | Tamarkin et al. | |
| 2008/0300229 A1 | 12/2008 | Willcox et al. | |
| 2009/0192201 A1 | 7/2009 | Selman-Housein Sosa | |
| 2010/0080768 A1 | 4/2010 | McGraw et al. | |
| 2010/0204298 A1 | 8/2010 | Levy | |
| 2010/0311843 A1 | 12/2010 | Johansen et al. | |
| 2011/0053898 A1 | 3/2011 | Mehta et al. | |
| 2012/0184511 A1 | 7/2012 | Goebel | |
| 2013/0245127 A1* | 9/2013 | Feuerherm ............... A61P 37/06 514/675 |
| 2013/0274197 A1 | 10/2013 | Glick | |
| 2014/0256824 A1 | 9/2014 | Johansen et al. | |
| 2015/0066474 A1 | 3/2015 | Yi et al. | |
| 2015/0258119 A1 | 9/2015 | Kandavalli et al. | |
| 2019/0076423 A1 | 3/2019 | Johansen et al. | |
| 2019/0167606 A1 | 6/2019 | Johansen | |
| 2019/0209585 A1 | 7/2019 | Johansen et al. | |
| 2019/0216815 A1 | 7/2019 | Johansen et al. | |
| 2020/0000744 A1 | 1/2020 | Hessman et al. | |
| 2020/0323793 A1 | 10/2020 | Johansen et al. | |

FOREIGN PATENT DOCUMENTS

| | | |
|---|---|---|
| AU | 2008200812 A1 | 3/2008 |
| CN | 1678323 A | 10/2005 |
| CN | 101849929 A | 10/2010 |
| CN | 102355889 A | 2/2012 |
| CN | 102802572 A | 11/2012 |
| CN | 103127140 A | 6/2013 |

(Continued)

OTHER PUBLICATIONS

Kalepu et al., Acta Pharmaceutica Sinica B 2013;3(6):361-372 (Year: 2013).*
SIMCO-ion application Note—Nitrogen Use with Medical Device Packaging—Preservation with Nitrogen Gas, 2012 (Year: 2012).*
Remington Pharmaceutical Sciences, Chapter 80, Mack Publishing Company, 1985 (Year: 1985).*
U.S. Appl. No. 16/084,845, filed Sep. 13, 2018, 2019-0076423, Allowed.
Albanesi, Keratinocytes in allergic skin diseases. Curr Opin Allergy Clin Immunol. Oct. 2010;10(5):452-6.
Albrightson et al., Selective inhibition of 5-lipoxygenase attenuates glomerulonephritis in the rat. Kidney Int. May 1994;45(5):1301-10.
Aldámiz-Echevarría et al., Effect of docosahexaenoic acid administration on plasma lipid profile and metabolic parameters of children with methylmalonic acidaemia. J Inherit Metab Dis. Feb. 2006;29(1):58-63.

(Continued)

Primary Examiner — San Ming R Hui
(74) Attorney, Agent, or Firm — McCarter & English, LLP; Steven G. Davis

(57) ABSTRACT

A pharmaceutical composition in the form of an emulsion, in particular an oil-in-water emulsion, comprising certain polyunsaturated long-chain ketones and polysorbate. The composition may be used to treat or prevent certain inflammatory or proliferative conditions.

16 Claims, No Drawings

(56) References Cited

FOREIGN PATENT DOCUMENTS

| | | | |
|---|---|---|---|
| CN | 103249408 A | 8/2013 | |
| CN | 104321053 A | 1/2015 | |
| CN | 104968349 A | 10/2015 | |
| EP | 0418680 A2 | 3/1991 | |
| EP | 0765661 A2 | 4/1997 | |
| EP | 0813403 A1 | 12/1997 | |
| EP | 1970049 A1 | 9/2008 | |
| EP | 2147910 A1 | 1/2010 | |
| EP | 2839833 A1 | 2/2015 | |
| JP | S61-018756 A | 1/1986 | |
| JP | H08-109128 A | 4/1996 | |
| JP | H09-143067 A | 6/1997 | |
| JP | 09-268153 | 10/1997 | |
| JP | H11-199493 A | 7/1999 | |
| JP | 2000-095683 A | 4/2000 | |
| JP | 2000-508645 A | 7/2000 | |
| JP | 2005-518419 A | 6/2005 | |
| JP | 2009-62316 A | 3/2009 | |
| JP | 2012-528813 A | 11/2012 | |
| JP | 2013-540713 A | 11/2013 | |
| JP | 2016-500092 A | 1/2016 | |
| WO | WO-1997/38688 A1 | 10/1997 | |
| WO | WO-1997/44026 A1 | 11/1997 | |
| WO | WO-1999/042101 A1 | 8/1999 | |
| WO | WO-2000/02561 A1 | 1/2000 | |
| WO | WO-2000/034348 A1 | 6/2000 | |
| WO | WO-2001/05761 A1 | 1/2001 | |
| WO | WO-2002/060535 A1 | 8/2002 | |
| WO | WO-2003/063878 A1 | 8/2003 | |
| WO | WO-2003/101487 A1 | 12/2003 | |
| WO | WO-2004/064715 A2 | 8/2004 | |
| WO | WO-2004/082402 A1 | 9/2004 | |
| WO | WO-2005/123060 A1 | 12/2005 | |
| WO | WO-2005/123061 A1 | 12/2005 | |
| WO | WO-2006/096579 A1 | 9/2006 | |
| WO | WO-2006/106438 A2 | 10/2006 | |
| WO | WO-2006/122806 A2 | 11/2006 | |
| WO | WO-2007/075841 A1 | 7/2007 | |
| WO | WO-2007/135518 A2 | 11/2007 | |
| WO | WO-2008/070129 A2 | 6/2008 | |
| WO | WO-2008/075366 A2 | 6/2008 | |
| WO | WO-2008/075978 A2 | 6/2008 | |
| WO | WO-2008/110815 A1 | 9/2008 | |
| WO | WO-2009/038671 A2 | 3/2009 | |
| WO | WO-2009/061208 A1 | 5/2009 | |
| WO | WO-2010/125340 A1 | 11/2010 | |
| WO | WO-2010/128401 A1 | 11/2010 | |
| WO | WO-2010/139482 A1 | 12/2010 | |
| WO | WO-2011/039365 A1 | 4/2011 | |
| WO | WO-2011/097276 A1 | 8/2011 | |
| WO | WO-2011/154004 A1 | 12/2011 | |
| WO | WO-2012/02688 A2 | 1/2012 | |
| WO | WO-2012/013331 A2 | 2/2012 | |
| WO | WO-2012/028688 A1 | 3/2012 | |
| WO | WO-2013/150386 A2 | 10/2013 | |
| WO | 2013/175174 A1 | 11/2013 | |
| WO | WO-2014/019841 A1 | 2/2014 | |
| WO | WO-2014/082960 A1 | 6/2014 | |
| WO | WO-2014/132134 A1 | 9/2014 | |
| WO | WO-2014/142995 A1 | 9/2014 | |
| WO | WO-2015/181135 A1 | 12/2015 | |
| WO | 2016/116634 A1 | 7/2016 | |
| WO | 2017/157955 A1 | 9/2017 | |
| WO | 2017/207818 A1 | 12/2017 | |
| WO | 2017/207819 A1 | 12/2017 | |
| WO | 2017/207820 A1 | 12/2017 | |
| WO | 2017/207821 A1 | 12/2017 | |

OTHER PUBLICATIONS

Alexander et al., Arachidonic acid induces ERK activation via Src SH2 domain association with the epidermal growth factor receptor. Kidney Int. May 2006;69(10):1823-32.

Allen et al., Systemic exposure, tolerability, and efficacy of pimecrolimus cream 1% in atopic dermatitis patients. Arch Dis Child. Nov. 2003;88(11):969-73.

Andersen et al., Elevated expression of human nonpancreatic phospholipase A2 in psoriatic tissue. Inflammation. Feb. 1994;18(1):1-12.

Anthonsen et al., Functional coupling between secretory and cytosolic phospholipase A2 modulates tumor necrosis factor-alpha- and interleukin-1 beta-induced NF-kappa B activation. J Biol Chem. Aug. 10, 2001;276(32):30527-36.

Atsumi et al., Distinct roles of two intracellular phospholipase A2s in fatty acid release in the cell death pathway. Proteolytic fragment of type IVA cytosolic phospholipase A2alpha inhibits stimulus-induced arachidonate release, whereas that of type VI Ca2+-independent phospholipase A2 augments spontaneous fatty acid release. J Biol Chem. Jun. 16, 2000;275(24):18248-58.

Blauvelt et al., 11. Allergic and immunologic diseases of the skin. J Allergy Clin Immunol. Feb. 2003;111(2 Suppl):S560-70.

British Association of Dermatologists, Methotrexate. Retrieved online at: http://www.bad.org.uk/for-the-public/patient-information-leaflets/methotrexate. 5 pages, (2015).

Brown et al., Protection of oxygen-sensitive pharmaceuticals with nitrogen. J Pharm Sci. Feb. 1969;58(2):242-5.

Cannon, Analog Design. Burger's Medicinal Chemistry and Drug Discovery. Fifth Edition, vol. I: Principles and Practice. Manfred E. Wolff (Ed.), John Wiley & Sons, Inc., New York. Chapter 19, pp. 783-802, (1995).

Cattell et al., Nitric oxide and glomerulonephritis. Kidney Int. Mar. 2002;61(3):816-21.

Chadban et al., Glomerulonephritis. Lancet. May 21-27, 2005;365(9473):1797-806.

Chen, Potential value and limitation of dual inhibitors of PI3K and mTOR in the treatment of cancer. Curr Cancer Drug Targets. Feb. 2013;13(2):117-20.

Costabile et al., The immunomodulatory effects of novel beta-oxa, beta-thia, and gamma-thia polyunsaturated fatty acids on human T lymphocyte proliferation, cytokine production, and activation of protein kinase C and MAPKs. J Immunol. Jan. 1, 2005;174(1):233-43.

Couser et al., Pathogenesis of glomerular damage in glomerulonephritis. Nephrol Dial Transplant. 1998;13 Suppl 1:10-5.

Cybulsky et al., Complement C5b-9 membrane attack complex increases expression of endoplasmic reticulum stress proteins in glomerular epithelial cells. J Biol Chem. Nov. 1, 2002;277(44):41342-51.

Cybulsky et al., Complement-induced phospholipase A2 activation in experimental membranous nephropathy. Kidney Int. Mar. 2000;57(3):1052-62.

Edmundson et al., Treatment of psoriasis with folic acid antagonists. AMA Arch Derm. Aug. 1958;78(2):200-3.

Edwards et al., Omega-3 Fatty Acids and PPARgamma in Cancer. PPAR Res. 2008;2008:358052. 14 pages.

Everyscience, Glossary-E. everyscience.com. 3 pages, (2004).

Flock et al., Syntheses of some polyunsaturated sulfur- and oxygen-containing fatty acids related to eicosapentaenoic and docosahexaenoic acids. Acta Chem Scand. Jun. 1999;53(6):436-45.

Flock et al., Syntheses of Some Sulfur-Containing Polyunsaturated Fatty Acids as Potential Lipoxygenase Inhibitors. Synthetic Communications. 2007;37(22):4005-4015.

Gautam et al., Identification of selective cytotoxic and synthetic lethal drug responses in triple negative breast cancer cells. Mol Cancer. May 10, 2016;15(1):34. 16 pages.

Gutfreund et al., Topical calcineurin inhibitors in dermatology. Part I: Properties, method and effectiveness of drug use. Postepy Dermatol Alergol. Jun. 2013;30(3):165-9.

Hagiwara et al., Eicosapentaenoic acid ameliorates diabetic nephropathy of type 2 diabetic KKAy/Ta mice: involvement of MCP-1 suppression and decreased ERK1/2 and p38 phosphorylation. Nephrol Dial Transplant. Mar. 2006;21(3):605-15.

Hansen et al., Syntheses of two cytotoxic polyunsaturated pyrrole metabolites of the marine sponge Mycale micracanthoxea. Tetrahedron Letters. Mar. 22, 2004;45(13):2809-2811.

(56) References Cited

OTHER PUBLICATIONS

Hao et al., Roles of lipid mediators in kidney injury. Semin Nephrol. May 2007;27(3):338-51.
Holmeide et al., Syntheses of some polyunsaturated trifluoromethyl ketones as potential phospholipase A2 inhibitors. J Chem Soc, Perkin Trans 1. 2000;1:2271-6.
Hua et al., AKT and cytosolic phospholipase A2a form a positive loop in prostate cancer cells. Curr Cancer Drug Targets. 2015;15(9):781-91.
Huber et al., Synovial fibroblasts: key players in rheumatoid arthritis. Rheumatology (Oxford). Jun. 2006;45(6):669-75.
Huwiler et al., The Omega3-polyunsaturated fatty acid derivatives AVX001 and AVX002 directly inhibit cytosolic phospholipase A(2) and suppress PGE(2) formation in mesangial cells. Br J Pharmacol. Dec. 2012;167(8):1691-701.
Ingber et al., A novel treatment of contact dermatitis by topical application of phospholipase A2 inhibitor: a double-blind placebo-controlled pilot study. Int J Immunopathol Pharmacol. Jan.-Mar. 2007;20(1):191-5.
Johannesdottir et al., Nonsteroidal anti-inflammatory drugs and the risk of skin cancer: a population-based case-control study. Cancer. Oct. 1, 2012;118(19):4768-76.
Johansen et al., Novel inhibitors of cytosolic Group IVA phospholipase A2 (cPLA2) ameliorate collagen induced arthritis. Br J Pharmacol. 2012;167:1691, Abstract No. 25.
Johansen et al., Phospholipase A2 in Psoriasis. Basic and Clinical Aspects in Inflammatory Diseases. Prog Surg. 1997;24:225-31.
Katagiri et al., Trifluoromethylated amino alcohol as chiral auxiliary for highly diastereoselective and fast Simmons-Smith cyclopropanation of allylic amine. Tetrahedron: Asymmetry. Apr. 18, 2006;17(8):1157-1160.
Kishida et al., Distinctive inhibitory activity of docosahexaenoic acid against sphingosine-induced apoptosis. Biochim Biophys Acta. Apr. 22, 1998;1391(3):401-8.
Kurogi, Mesangial cell proliferation inhibitors for the treatment of proliferative glomerular disease. Med Res Rev. Jan. 2003;23(1):15-31.
Kusunoki et al., Pro-apoptotic effect of nonsteroidal anti-inflammatory drugs on synovial fibroblasts. Mod Rheumatol. 2008;18(6):542-51.
Lamothe et al., Efficacy of giripladib, a novel inhibitor of cytosolic phospholipase A2alpha, in two different mouse models of rheumatoid arthritis. Clin Immunol. 2008;127:889-90. Abstract Sa.29.
Larsen et al., Polyunsaturated thia- and oxa-fatty acids: incorporation into cell-lipids and their effects on arachidonic acid- and eicosanoid synthesis. Biochim Biophys Acta. Oct. 18, 1997;1348(3):346-54.
Lianos et al., Biosynthesis and role of arachidonic acid metabolites in glomerulonephritis. Nephron. 1984;37(2):73-7.
Liu et al., EGFR signaling is required for TGF-beta 1 mediated COX-2 induction in human bronchial epithelial cells. Am J Respir Cell Mol Biol. Nov. 2007;37(5):578-88.
Ma et al., 12/15-lipoxygenase inhibitors in diabetic nephropathy in the rat. Prostaglandins Leukot Essent Fatty Acids. Jan. 2005;72(1):13-20.
Maira et al., Identification and characterization of NVP-BEZ235, a new orally available dual phosphatidylinositol 3-kinase/mammalian target of rapamycin inhibitor with potent in vivo antitumor activity. Mol Cancer Ther. Jul. 2008;7(7):1851-63.
Malaviya et al., Targeting cytosolic phospholipase A2 by arachidonyl trifluoromethyl ketone prevents chronic inflammation in mice. Eur J Pharmacol. Jun. 13, 2006;539(3):195-204.
Matsuzawa et al., Activation of cytosolic phospholipase A2alpha by epidermal growth factor (EGF) and phorbol ester in HeLa cells: different effects of inhibitors for EGF receptor, protein kinase C, Src, and C-Raf. J Pharmacol Sci. Oct. 2009;111(2):182-92.
McKew et al., Indole cytosolic phospholipase A2 alpha inhibitors: discovery and in vitro and in vivo characterization of 4-{3-[5-chloro-2-(2-{[(3,4-dichlorobenzyl)sulfonyl]amino}ethyl)-1-(diphenylmethyl)-1H-indol-3-yl]propyl}benzoic acid, efipladib. J Med Chem. Jun. 26, 2008;51(12):3388-413.
Miller et al., Dietary supplementation with ethyl ester concentrates of fish oil (n-3) and borage oil (n-6) polyunsaturated fatty acids induces epidermal generation of local putative anti-inflammatory metabolites. J Invest Dermatol. Jan. 1991;96(1):98-103.
Mizoguchi et al., Cyclosporin ointment for psoriasis and atopic dermatitis. Lancet. May 2, 1992;339(8801):1120.
Nakamura et al., Effects of eicosapentaenoic acids on oxidative stress and plasma fatty acid composition in patients with lupus nephritis. In Vivo. Sep.-Oct. 2005;19(5):879-82.
Ono et al., Characterization of a novel inhibitor of cytosolic phospholipase A2alpha, pyrrophenone. Biochem J. May 1, 2002;363(Pt 3):727-35.
Papanikolaou, Alteration of mercuric chloride-induced autoimmune glomerulonephritis in brown-Norway rats by herring oil, evening primrose oil and OKY-046 a selective TXA-synthetase inhibitor. Prostaglandins Leukot Med. May 1987;27(2-3):129-49.
Proudman et al., Fish oil in recent onset rheumatoid arthritis: a randomised, double-blind controlled trial within algorithm-based drug use. Ann Rheum Dis. Jan. 2015;74(1):89-95.
Ringbom et al., Cox-2 inhibitory effects of naturally occurring and modified fatty acids. J Nat Prod. Jun. 2001;64(6):745-9.
Robinson et al., Suppression of autoimmune disease by dietary n-3 fatty acids. J Lipid Res. Aug. 1993;34(8):1435-44.
Rodriguez et al., Hyperosmotic stress induces phosphorylation of cytosolic phospholipase A(2) in HaCaT cells by an epidermal growth factor receptor-mediated process. Cell Signal. Oct. 2002;14(10):839-48.
Ryan et al., The Treatment of Psoriasis With Folic Acid Antagonists. Br J Dermatol. Dec. 1964;76:555-64.
Sakaguchi et al., Truncation of annexin A1 is a regulatory lever for linking epidermal growth factor signaling with cytosolic phospholipase A2 in normal and malignant squamous epithelial cells. J Biol Chem. Dec. 7, 2007;282(49):35679-86.
Sandri et al., Syntheses of all-(Z)-5,8,11,14,17-Eicosapentaenoic Acid and all-(Z)-4,7,10,13,16,19-Docosahexaenoic Acid from (Z)-1,1,6,6-tetraisopropoxy-3-hexene. J Org Chem. 1995;60(20):6627-30.
Schalkwijk et al., Maximal epidermal growth-factor-induced cytosolic phospholipase A2 activation in vivo requires phosphorylation followed by an increased intracellular calcium concentration. Biochem J. Jan. 1, 1996;313 ( Pt 1):91-6.
Scheinfeld, The use of topical tacrolimus and pimecrolimus to treat psoriasis: a review. Dermatol Online J. Jul. 15, 2004;10(1):3. 5 pages.
Scuderi et al., Expression of Ca(2+)-independent and Ca(2+)-dependent phospholipases A(2) and cyclooxygenases in human melanocytes and malignant melanoma cell lines. Biochim Biophys Acta. Oct. 2008;1781 (10):635-42.
Sene et al., Silicones as Excipients for Topical Pharmaceutical Applications. The Silky Touch Product Family from Dow Corning. Dow Corning Corporation, retrieved online at: www.dowcorning.co.jp/ja_JP/content/published.lit/52-1034-01.pdf. 12 pages (2002).
Sheridan, The most common chemical replacements in drug-like compounds. J Chem Inf Comput Sci. Jan.-Feb. 2002;42(1):103-8.
Shi et al., Attenuation of mycotoxin-induced IgA nephropathy by eicosapentaenoic acid in the mouse: dose response and relation to IL-6 expression. J Nutr Biochem. Oct. 2006;17(10):697-706.
Six et al., Structure-activity relationship of 2-oxoamide inhibition of group IVA cytosolic phospholipase A2 and group V secreted phospholipase A2. J Med Chem. Aug. 23, 2007;50(17):4222-35.
Six et al., The expanding superfamily of phospholipase A(2) enzymes: classification and characterization. Biochim Biophys Acta. Oct. 31, 2000;1488(1-2):1-19.
Sjursen et al., Secretory and cytosolic phospholipase A(2)regulate the long-term cytokine-induced eicosanoid production in human keratinocytes. Cytokine. Aug. 2000;12(8):1189-94.
Sommerfelt et al., Cytosolic phospholipase A2 regulates TNF-induced production of joint destructive effectors in synoviocytes. PLoS One. Dec. 12, 2013;8(12):e83555. 8 pages.

(56) References Cited

OTHER PUBLICATIONS

Stewart, Calcipotriol for psoriasis, Dovonex. Patient, retrieved online at: https:patient.info/medicine/calcipotriol-for-psoriasis-dovonex. 3 pages, (2015).
Stewart, Tacalcitol for psoriasis, Curatoderm. Patient, retrieved online at: https://patient.info/medicine/tacalcitol-for-psoriasis-curatoderm. 6 pages, (2015).
Sundler et al., Acyl-chain selectivity of the 85 kDa phospholipase A2 and of the release process in intact macrophages. Biochem J. Jul. 15, 1994;301 ( Pt 2):455-8.
Tai et al., Cytosolic phospholipase A2 alpha inhibitor, pyrroxyphene, displays anti-arthritic and anti-bone destructive action in a murine arthritis model. Inflamm Res. Jan. 2010;59(1):53-62.
Thommesen et al., Selective inhibitors of cytosolic or secretory phospholipase A2 block TNF-induced activation of transcription factor nuclear factor-kappa B and expression of ICAM-1. J Immunol. Oct. 1, 1998;161(7):3421-30.
WebMD, Sking Problems & Treatments Health Center, Psoriasis Overview. Retrieved online at: http://www.webmd.com/skin-problems-and-treatments/psoriasis-overview. 2 pages, Sep. 1, 2005.
Wen et al., Critical role of arachidonic acid-activated mTOR signaling in breast carcinogenesis and angiogenesis. Oncogene. Jan. 10, 2013;32(2):160-70.
Yan et al., Cytosolic Phospholipase A2 is Involved in Epidermal Growth Factor and Fetal Bovine Serum-induced Proliferation in Hela Cells. Chinese Doctoral Dissertation & Master's Theses. 68 pages (2005).
Zulfakar et al., Enhanced topical delivery and ex vivo anti-inflammatory activity from a betamethasone dipropionate formulation containing fish oil. Inflamm Res. Jan. 2010;59(1):23-30.
European Office Action for Application No. 11757227.1, dated Mar. 19, 2014. 8 pages.
International Search Report and Written Opinion for Application No. PCT/EP2010/003384, dated Aug. 6, 2010.
International Search Report and Written Opinion for Application No. PCT/EP2011/065123, dated Dec. 23, 2011. 14 pages.
International Search Report and Written Opinion for Application No. PCT/EP2013/074612, dated Mar. 18, 2014.
International Search Report and Written Opinion for Application No. PCT/EP2017/056022, dated Jul. 5, 2017. 17 pages.
International Search Report and Written Opinion for Application No. PCT/EP2017/063625, dated Sep. 8, 2017, 11 pages.
International Search Report and Written Opinion for Application No. PCT/EP2017/063627, dated Sep. 8, 2017, 11 pages.
International Search Report and Written Opinion for Application No. PCT/EP2017/063628, dated Sep. 8, 2017, 12 pages.
International Search Report and Written Opinion for Application No. PCT/EP2017/063629, dated Sep. 8, 2017, 12 pages.
International Search Report and Written Opinion for Application No. PCT/EP2017/073951, dated Nov. 13, 2017, 13 pages.
International Search Report and Written Opinion for Application No. PCT/EP2017/073958, dated Dec. 5, 2017, 16 pages.
Japanese Office Action for Application No. 2015-543453, dated Jul. 13, 2017, 5 pages. English translation only.
American Thoracic Society, Idiopathic pulmonary fibrosis: diagnosis and treatment. International consensus statement. American Thoracic Society (ATS), and the European Respiratory Society (ERS). Am J Respir Crit Care Med. Feb. 2000;161(2 Pt 1):646-64.
Ashcroft et al., Simple method of estimating severity of pulmonary fibrosis on a numerical scale. J Clin Pathol. Apr. 1988;41(4):467-70.
Carlson et al., Wound splinting regulates granulation tissue survival. J Surg Res. Mar. 2003;110(1):304-9.
Dendooven et al., Oxidative stress in obstructive nephropathy. Int J Exp Pathol. Jun. 2011;92(3):202-10.
Eddy et al., Investigating mechanisms of chronic kidney disease in mouse models. Pediatr Nephrol. Aug. 2012;27(8):1233-47.
Gu et al., Application of topical calcineurin inhibitor in the treatment of skin diseases. World Clinical Drugs. 2014:35(3):6 pages.
Halper et al., Basic Components of Connective Tissues and Extracellular Matrix: Elastin, Fibrillin, Fibulins, Fibrinogen, Fibronectin, Laminin, Tenascins and Thrombospondins. Progress in Heritable Soft Connective Tissue Diseases, Advances in Experimental Medicine and Biology, vol. 802. Springer. Chapter 3, pp. 31-47, (2014).
Hinz et al., The myofibroblast: one function, multiple origins. Am J Pathol. Jun. 2007;170(6):1807-16.
Johansen et al., Mutations in MBOAT7 links cortical polymicrogyria to lipid remodeling. Lipid Maps Annual Meeting 2015: Lipidomics Impact on Cancer, Metabolic, and Inflammatory Diseases, 12th Annual Meeting. Retrieved online at: http://www.lipidmaps.org/meetings/2015annual/posters.pdf. p. 17, Poster 16. May 12-13, 2015.
Khan et al., Cytosolic Phospholipase A2alpha is Essential for Renal Dysfunction and End-Organ Damage Associated With Angiotensin II-Induced Hypertension. Am J Hypertens. Feb. 2016;29(2):258-65.
Liu et al., The Bleomycin Model of Pulmonary Fibrosis. Methods Mol Biol. 2017;1627:27-42.
Mason et al., Lung transplantation for idiopathic pulmonary fibrosis. Ann Thorac Surg. Oct. 2007;84(4):1121-8.
Noble et al., Idiopathic pulmonary fibrosis: new insights into pathogenesis. Clin Chest Med. Dec. 2004;25(4):749-58.
Rayego-Mateos et al., Connective tissue growth factor induces renal fibrosis via epidermal growth factor receptor activation. J Pathol. Feb. 2018;244(2):227-241.
Selman et al., Idiopathic pulmonary fibrosis: prevailing and evolving hypotheses about its pathogenesis and implications for therapy. Ann Intern Med. Jan. 16, 2001;134(2):136-51.
Tomasek et al., Myofibroblasts and mechano-regulation of connective tissue remodelling. Nat Rev Mol Cell Bio. 2002;3:349-63.
Werner et al., Regulation of wound healing by growth factors and cytokines. Physiol Rev. Jul. 2003;83(3):835-70.
Zhao et al., Involvement of cytosolic phospholipase A2 alpha signalling pathway in spontaneous and transforming growth factor-beta-induced activation of rat hepatic stellate cells. Liver Int. Nov. 2011;31(10):1565-73.
U.S. Appl. No. 13/957,899, dated Aug. 2, 2013, U.S. Pat. No. 8,865,768, Issued.
U.S. Appl. No. 16/171,925, filed Oct. 26, 2018, Abandoned.
U.S. Appl. No. 16/436,419, filed Jun. 10, 2019, Abandoned.
U.S. Appl. No. 16/117,148, filed Aug. 30, 2018, U.S. Pat. No. 10,758,499, Issued.
U.S. Appl. No. 16/389,453, filed Apr. 19, 2019, Abandoned.
U.S. Appl. No. 16/084,845, filed Sep. 13, 2018, U.S. Pat. No. 10,953,004, Issued.
U.S. Appl. No. 16/306,126, filed Nov. 30, 2018, 2020-0330399, Abandoned.
U.S. Appl. No. 16/306,106, filed Nov. 30, 2018, 2019-0209585, Abandoned.
U.S. Appl. No. 16/306,161, filed Nov. 30, 2018, 2020-0323793, Abandoned.
U.S. Appl. No. 16/306,092, filed Nov. 30, 2018, 2019-0216815, Abandoned.
U.S. Appl. No. 16/334,916, filed Mar. 20, 2019, 2020-0000744, Published.
U.S. Appl. No. 16/622,833, filed Dec. 13, 2019, Pending.
Zhu, Pharmacy, Yaojixue, No. 4 Military Medical University. pp. 316-317, (2007).
International Search Report and Written Opinion for Application No. PCT/EP2018/066028, dated Aug. 31, 2018, 12 pages.
U.S. Appl. No. 10/502,414, filed Jan. 11, 2005, U.S. Pat. No. 7,687,543, Issued.
U.S. Appl. No. 12/713,917, filed Feb. 26, 2010, U.S. Pat. No. 8,524,776, Issued.
U.S. Appl. No. 13/957,899, filed Aug. 2, 2013, U.S. Pat. No. 8,865,768, Issued.
U.S. Appl. No. 14/487,382, filed Sep. 16, 2014, U.S. Pat. No. 9,375,409, Issued.
U.S. Appl. No. 15/166,121, filed May 26, 2016, Abandoned.
U.S. Appl. No. 15/404,536, filed Jan. 12, 2017, Abandoned.
U.S. Appl. No. 15/686,378, filed Aug. 25, 2017, Abandoned.
U.S. Appl. No. 15/907,969, filed Feb. 28, 2018, Abandoned.
U.S. Appl. No. 16/171,925, filed Oct. 26, 2018, Pending.
U.S. Appl. No. 16/436,419, filed Jun. 10, 2019, Pending.

(56) References Cited

OTHER PUBLICATIONS

U.S. Appl. No. 12/794,367, filed Jun. 4, 2010, U.S. Pat. No. 8,796,251, Issued.
U.S. Appl. No. 14/200,238, filed Mar. 7, 2014, U.S. Pat. No. 9,187,396, Issued.
U.S. Appl. No. 13/783,088, filed Mar. 1, 2013, U.S. Pat. No. 9,682,930, Issued.
U.S. Appl. No. 15/623,962, filed Jun. 15, 2017, Abandoned.
U.S. Appl. No. 14/647,765, filed May 27, 2015, U.S. Pat. No. 10,085,952, Issued.
U.S. Appl. No. 16/117,148, filed Aug. 30, 2018, 2019-0167606, Published.
U.S. Appl. No. 15/360,084, filed Nov. 23, 2016, U.S. Pat. No. 10,085,953, Issued.
U.S. Appl. No. 16/117,175, filed Aug. 30, 2018, Abandoned.
U.S. Appl. No. 16/389,453, filed Apr. 19, 2019, Pending.
U.S. Appl. No. 16/084,845, filed Sep. 13, 2018, 2019-0076423, Published.
U.S. Appl. No. 16/306,126, filed Nov. 30, 2018, Pending.
U.S. Appl. No. 16/306,106, filed Nov. 30, 2018, 2019-0209585, Published.
U.S. Appl. No. 16/306,161, filed Nov. 30, 2018, Pending.
U.S. Appl. No. 16/306,092, filed Nov. 30, 2018, 2019-0216815, Published.
U.S. Appl. No. 16/334,916, filed Mar. 20, 2019, Pending.

* cited by examiner

PHARMACEUTICAL COMPOSITION

This invention relates to a pharmaceutical composition in the form of an emulsion, in particular an oil-in-water emulsion, comprising certain polyunsaturated long-chain ketones. The invention also relates to methods of treating or preventing certain inflammatory or proliferative conditions using the composition of the invention.

BACKGROUND

Certain polyunsaturated long chain ketones are described in various prior art references for the treatment of conditions including psoriasis, dermatitis, skin cancer, glomerulonephritis and rheumatoid arthritis (See EP-A-1469859, WO2010/139482, WO2012/028688, WO2014/082960 and WO2015/181135).

The polyunsaturated long chain ketones which are described in these references have amphiphilic character but are primarily hydrophobic and therefore insoluble in water. The lack of water solubility limits the bioavailability of the compounds and limits the ability of the skilled person to administer a useful dose of these compounds to a patient. In particular, the lack of water solubility limits the ability of the skilled person to administer the compounds parenterally, e.g. intravenously, intramuscularly or subcutaneously to a patient.

A further problem with the polyunsaturated ketone compounds of the invention is that they are susceptible to degradation. Any formulation of these compounds should also ensure that the compounds remain stable for a prolonged period.

The present inventors sought a solution to the problem of parenteral administration of these compounds and the problem of their stability. The inventors have now found that these compounds can be advantageously formulated as an emulsion, in particular an oil-in-water emulsion. It is envisaged that the use of an emulsion may lead to a prolonged shelf life and should also allow administration of the compound of the invention by parenteral routes such as intravenously (i.v.), intramuscularly (i.m.) and sub-cutaneously (s.c.).

SUMMARY OF INVENTION

Thus, viewed from one aspect the invention provides a composition in the form of an aqueous emulsion comprising:
(i) a compound of formula (I)

$$R\text{-}L\text{-}CO\text{---}CF_3 \qquad (I)$$

wherein R is an unsubstituted linear $C_{10\text{-}24}$ unsaturated hydrocarbon group, said hydrocarbon group comprising at least 4 non-conjugated double bonds;
L is a linking group forming a bridge of 2 to 5 atoms between the R group and the carbonyl CO wherein L comprises at least one of S, SO, $SO_2$ in the backbone of the linking group;
or a salt thereof;
(ii) a polysorbate and/or poloxamer surfactant;
(iii) optionally a triglyceride; and
(iv) a buffer, chelating agent and/or a lipid dissolvable antioxidant.

Viewed from another aspect the invention provides a composition in the form of an oil-in-water emulsion comprising:
(i) a compound of formula (I)

$$R\text{-}L\text{-}CO\text{---}CF_3 \qquad (I)$$

wherein R is a linear $C_{10\text{-}24}$ unsaturated hydrocarbon group, said hydrocarbon group comprising at least 4 non-conjugated double bonds;
L is a linking group forming a bridge of 2 to 5 atoms between the R group and the carbonyl CO wherein L comprises at least one of S, SO, $SO_2$ in the backbone of the linking group;
or a salt thereof;
(ii) a polysorbate and/or poloxamer surfactant;
(iii) a triglyceride; and
(iv) a buffer and/or chelating agent.

Viewed from another aspect the invention provides a composition in the form of an oil-in-water emulsion comprising:
(i) a compound of formula (I)

$$R\text{-}L\text{-}CO\text{---}CF_3 \qquad (I)$$

wherein R is a linear $C_{10\text{-}24}$ unsaturated hydrocarbon group, said hydrocarbon group comprising at least 4 non-conjugated double bonds;
L is a linking group forming a bridge of 2 to 5 atoms between the R group and the carbonyl CO wherein L comprises at least one of S, SO, $SO_2$ in the backbone of the linking group;
or a salt thereof;
(ii) a polysorbate surfactant;
(iii) a triglyceride; and
(iv) a buffer.

Viewed from another aspect the invention provides a method of treating or preventing an inflammatory or proliferative condition comprising administering to an animal, preferably a mammal, in need thereof, e.g. human, an effective amount of a composition as hereinbefore defined.

Viewed from another aspect the invention provides use of an emulsion as hereinbefore described in the manufacture of a medicament for use in the treatment or prevention of an inflammatory or proliferative condition in an animal.

Viewed from another aspect the invention provides a composition as hereinbefore described for use in the treatment or prevention of an inflammatory or proliferative condition in an animal.

Viewed from another aspect the invention provides an article of manufacture comprising a container carrying the composition as hereinbefore defined.

Definitions

The term "compound of the invention" relates to an active agent of formula (I), or a salt or solvate thereof, in particular a compound A or B as herein defined.

The terms "oil-in-water formulation" and "oil-in-water emulsion" are used interchangeably to describe a dispersion in an aqueous phase. The "dispersed phase" comprises the compound of the invention in an aqueous phase (the "continuous phase").

The term "nanoemulsion" relates to an oil-in-water emulsion in which the dispersed oil phase comprises "nanodroplets" which are hydrophobic droplets having a diameter of nanometers, i.e. from 1 to under 1000 nm, in a continuous aqueous phase.

DETAILED DESCRIPTION

This invention concerns emulsions, especially oil-in-water emulsions, comprising compounds of formula (I) or salts thereof and their use in the treatment or prevention of various conditions such as inflammatory or proliferative conditions. The compound of the invention is preferably present in the dispersed phase of the oil-in-water emulsion.

Compounds of the Invention

The emulsion comprises at least one compound of formula (I):

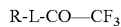   (I)

Preferably, only one compound of formula (I) is present in the emulsions of the invention.

The group R preferably comprises 5 to 9 double bonds, preferably 5 to 8 double bonds, e.g. 5 to 7 double bonds such as 5 or 6 double bonds. These bonds should be non-conjugated. It is also preferred if the double bonds do not conjugate with the carbonyl functionality.

The double bonds present in the group R may be in the cis or trans configuration however, it is preferred if the majority of the double bonds present (i.e. at least 50%) are in the cis configuration. In further advantageous embodiments all the double bonds in the group R are in the cis configuration or all double bonds are in the cis configuration except the double bond nearest the carbonyl group which may be in the trans configuration.

The group R may have between 10 and 24 carbon atoms, preferably 17 to 19 carbon atoms.

The R group is unsubstituted. The R group is linear. It preferably derives from a natural source such as a long chain fatty acid or ester.

The linking group L provides a bridging group of 2 to 5 backbone atoms, preferably 2 to 4 backbone atoms between the R group and the carbonyl. The atoms in the backbone of the linker may be carbon and heteroatoms but will include at least one of S, SO, or $SO_2$. The linking group is preferably unsubstituted. It is preferably linear.

Preferred components of the linking group are —$CH_2$—, —S—, —SO—, and —$SO_2$— which can be combined with each other in any (chemically meaningful) order to form the linking group. Thus, by using two methylene groups and an —S— group the linker —$SCH_2CH_2$— is formed.

The linking group L contains at least one heteroatom in the backbone. It is also preferred if the first backbone atom of the linking group attached to the R group is a heteroatom or group of heteroatoms selected from —S—, —SO—, and —$SO_2$.

It is highly preferred if the linking group L contains at least one —$CH_2$— link in the backbone. Ideally the atoms of the linking group adjacent the carbonyl are —$CH_2$—.

It is preferred if a heteroatom —S—, —SO— or —$SO_2$ is positioned α, β, γ, or δ to the carbonyl, preferably β or γ to the carbonyl.

Highly preferred linking groups therefore are —$SCH_2$—, —$SOCH_2$—, or —$SO_2CH_2$—

Preferred compounds of formula (I) are those of formula (I')

R—Y1-$CH_2$—CO—$CF_3$   (I')

wherein R is as hereinbefore defined; and
Y1 is selected from S, SO or $SO_2$.

Highly preferred compounds for use in the invention are depicted below.

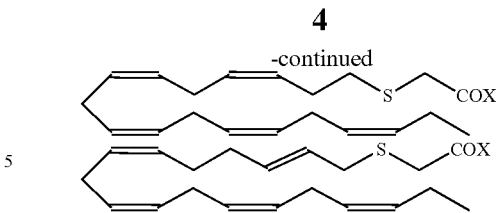

where X is $CF_3$.

The following compounds, especially compound B, are highly preferred for use in the invention:

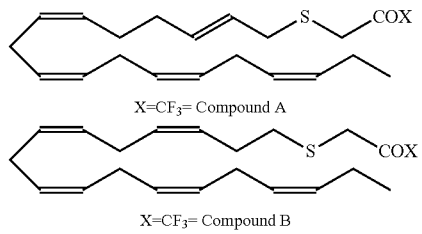

X=$CF_3$= Compound A

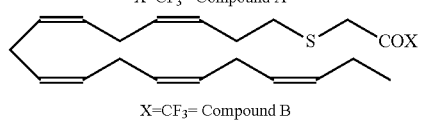

X=$CF_3$= Compound B

Where possible, the compounds can be present in the emulsion as a salt or solvate. Preferably however, no such form is used.

Compounds of formula (I) may be manufactured using known chemical synthetic routes found in J. Chem. Soc., Perkin Trans 1, 2000, 2271-2276 or J. Immunol., 1998, 161, 3421.

It has now surprisingly been established that compounds having the structures described herein can be formulated as an emulsion, such as an oil-in-water emulsion, preferably a nanoemulsion, when combined with a polysorbate or poloxamer surfactant and optionally a triglyceride excipient. It has surprisingly been found that emulsions of the compounds described have excellent long term storage stability, particularly at refrigerator or freezer temperatures.

Without wishing to be bound by theory, the compounds described have amphiphilic character but are primarily hydrophobic. It is thought that as a result of these characteristics, the compounds of the invention are capable of forming ordered nanostructures, such as micelles, in an aqueous environment. These micelles are not a structure which would usually be adopted by the compounds in pure form or in conventional solvents. The inventors have now established that particularly stable structures, such as mixed micelles, comprising both the compound of the invention and the triglyceride excipient have excellent storage stability.

The amount of compound of the invention in the emulsion can vary. Suitable amounts include 1 to 500 mg, such as 1 to 300 mg, more preferably 1 to 250 mg, especially 1 to 150 mg, especially 1 to 100 mg per ml of emulsion. Values of 1 to 20 mg/ml, such as 1 to 10 mg/ml are especially preferred.

Polysorbate and/or Poloxamer Surfactant

The emulsions of the invention include a polysorbate and/or poloxamer surfactant. Appropriate levels of surfactant are 0.1 to 100 mg, such as 0.1 to 25 mg of surfactant in 1 mL of emulsion, preferably 0.2 to 20 mg, such as 0.5 to 15 mg, and especially 1 to 12 mg per mL of emulsion.

Polysorbate surfactants are based on sorbitan, which is a sugar derivative having four OH groups per molecule. Suitable surfactants are those in which the OH groups of sorbitan are capped with repeating ethoxy groups and one of the repeating ethoxy groups is itself capped with a fatty acid ester.

Polysorbates such as polysorbate 20, 40, 60 or 80 could be used. A particularly preferred surfactant is Polysorbate 80.

Alternatively, the surfactant may be a poloxamer. The term "poloxamer" is a term of the art and describes block polymers having a central block of polyoxypropylene and two outer blocks of polyoxyethylene. A particularly preferred poloxamer is Poloxamer 188.

In general, polyethoxylated non-ionic surfactants are suitable herein.

It is possible to use a mixture of surfactants such as two or more polysorbates, two or more poloxamers or a poloxamer and a polysorbate. Preferably, one surfactant is used.

In a preferred embodiment, the active compound is compound A or B defined above and the surfactant is a polysorbate, especially polysorbate 80.

Triglyceride Excipient

In addition to the surfactant, compositions of the invention can comprise one or more triglycerides, preferably one triglyceride. The triglyceride component ideally acts to dissolve the compound of the invention to encourage formation of micelles in an aqueous environment in the presence of the surfactant.

Where the triglyceride forms a minor component, it can be seen assisting in the formation of micelles and/or improving the stability of micelles formed by the compound of the invention. In the event that the excipient forms a major component (i.e. is present in a greater amount percentage by weight than the compound) it can be seen as a type of carrier for the compound.

The triglyceride is preferably a medium chain triglyceride (MCT), which are compounds having a glycerol backbone esterified with three C6-C12 fatty acids, especially caproic acid (C6:0), caprylic acid (C8:0), capric acid (C10:0) or lauric acid (C12:0). Suitable sources include corn oil, sunflower oil, peanut oil, olive oil, coconut oil, or most preferably MCT oil, which is a highly purified coconut oil.

Suitable levels of excipient are 0.1 to 500 mg, such as 0.1 to 25 mg of triglyceride in 1 mL of emulsion, preferably 0.2 to 20 mg, such as 0.5 to 15 mg, and especially 1 to 12 mg per mL of emulsion. Where mixtures of triglycerides are used as the excipient, these levels relate to the mixture of triglycerides.

In a preferred embodiment the compound is compound A or B as herein defined and the triglyceride is MCT oil. In a yet even more preferred embodiment the compound is A or B, the triglyceride is MCT oil, and the surfactant is Polysorbate 80.

In a preferred embodiment, there can be
(i) 1 to 20 mg/ml of a compound of formula (I) as hereinbefore described;
(ii) 1 to 20 mg/ml of a polysorbate and/or poloxamer surfactant; and optionally
(iii) 1 to 20 mg/ml of a triglyceride.

In a preferred embodiment, there can be
(i) 1 to 10 mg/ml of a compound of formula (I) as hereinbefore described;
(ii) 1 to 10 mg/ml of a polysorbate and/or poloxamer surfactant, e.g. polysorbate 80; and
(iii) 1 to 10 mg/ml of a triglyceride, e.g. MCT oil.

Ideally the balance of the emulsion is the buffer and/or chelating agent (and water).

Other Components

The emulsion of the invention includes a buffer, a lipid soluble antioxidant and/or chelating agent. Preferably, the emulsion of the invention comprises a buffer and/or a chelating agent. Ideally, the emulsion contains a buffer.

Ideally any buffer present will maintain the pH of the emulsion at around 7. Preferably the buffer maintains the pH of the emulsion in the range of 6 to 9, preferably 6 to 8, more preferably pH 7±0.5. Any suitable buffer may be used. However, a particularly preferred buffer is citrate buffer. Ideally, the emulsion is isotonic. The molarity of the buffer may be 5 to 20 mmol, such as 10 mmol.

Certain buffers such as citrate buffer may also bind traces of metals and thereby reduce oxidative degradation of the compound of the invention.

Alternatively or as well as the buffer, a separate chelating agent, e.g. EDTA or a salt thereof, may also be present.

The compositions may also comprise a lipid dissolvable antioxidant such as tocopherol or other vitamin E analogue.

The emulsions of the invention may also contain other active components, e.g. other drugs, although this is not preferred.

In a most preferred embodiment, the emulsion consists of the compound of the invention, the polysorbate or poloxamer surfactant, the triglyceride excipient and a buffer and/or chelating agent (along with water).

In a further preferred embodiment, the invention provides a pharmaceutical composition in the form of an aqueous emulsion comprising from about 1 mg to about 500 mg of a compound of formula A or B

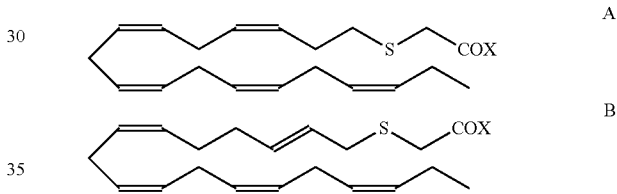

where X is $CF_3$;
about 0.1 mg to about 10 mg of Polysorbate 80,
about 0.1 mg to about 10 mg MCT oil; and
a buffering agent, e.g. a citrate buffer.

Nanoemulsions

In a preferred embodiment, the emulsion of the invention is a nanoemulsion. The nanoemulsion comprises a dispersed oil phase and a continuous aqueous phase. The particles of the dispersed phase have an average particle size of from 1 to less than 1000 nm, preferably 5 to 200 nm. Particle size can be measured by routine means, e.g. by microscopy (TEM, SEM, AFM), light scattering techniques (Photon Correlation Spectroscopy (PCS)), etc.

The emulsions of the invention, such as the nanoemulsions of the invention, are generally formed by mixing the components (compound, surfactant, excipient and any additives) and making the volume up a predetermined level using water for injection (WFI). It may be that the compound of the invention is precontacted with the triglyceride before addition of the surfactant. The water will typically be added containing the buffer/chelating agent.

The mixture of components can then be agitated, e.g. using a shaker and/or with sonication. The emulsion may be sterile filtered after production.

Stability

The compounds present in compositions of the invention can decompose into a variety of by-products. In stability studies, the inventors have determined that particularly notable by-products are sulfoxide and thiol compounds derived from the compound of the invention. The generation of by-products can be reduced by formulation of the compounds as an emulsion as described herein.

As is illustrated by the examples, emulsions comprising a surfactant and an excipient of the invention have excellent long term storage stability. By "stable" it is meant that the compound peak area, as measured by chromatograph, is reduced by no more than 20% after 1 month of storage at 5° C., and preferably no more than 20% reduction after 3 months of storage at 5° C., preferably no more than 20% reduction after 6 months of storage at 5° C. in an inert atmosphere.

Preferably the peak area is reduced by no more than 10% after 1 month, 3 months or 6 months of storage at 5° C. Most preferably the peak area is reduced by no more than 5% after 1 month, 3 months or 6 months of storage at 5° C. in an inert atmosphere.

Preferably the compound peak area, as measured by chromatograph, is reduced by no more than 5% after 1 month of storage at −20° C., and preferably no more than 5% reduction after 3 months of storage at −20° C., preferably after 6 months of storage at −20° C. in an inert atmosphere. Preferably the peak area is reduced by no more than 3% after 1 month, 3 months or 6 months of storage at −20° C. in an inert atmosphere. Most preferably the peak area is reduced by no more than 2% after 1 month, 3 months or 6 months of storage at −20° C. in an inert atmosphere.

Article

The compositions of the invention are suitable for administration to a patient. In order to administer the emulsion, the composition may be provided in a container holding the emulsion. The container may form part of a kit along with instructions for administration of the composition. Where the administration route is parenteral such as subcutaneous, intramuscular or intravenous, the container may be an administration device comprising a pre-determined amount of the formulation, e.g. a pre-filled syringe.

The container preferably comprises an inert gas added to displace air and hence maximise storage stability.

Suitable containers may have a volume up to 10 ml, such as 1 to 10 ml.

Treatment

The emulsions of the invention are proposed for use in the treatment or prevention of inflammatory disorders or proliferative conditions including psoriasis, glomerulonephritis, lupus nephritis, diabetic nephropathy, rheumatoid arthritis, dermatitis and cancers such as skin cancer. In particular, the emulsions of the invention are proposed for use in the treatment or prevention of inflammatory disorders or proliferative conditions including diabetic nephropathy and arthritis such as rheumatoid arthritis.

By treating or treatment is meant at least one of:
(i). inhibiting the disease i.e. arresting, reducing or delaying the development of the disease or a relapse thereof or at least one clinical or subclinical symptom thereof, or
(ii). relieving or attenuating one or more of the clinical or subclinical symptoms of the disease.

By prevention is meant (i) preventing or delaying the appearance of clinical symptoms of the disease developing in a mammal The benefit to a subject to be treated is either statistically significant or at least perceptible to the patient or to the physician. In general a skilled man can appreciate when "treatment" occurs. It is particularly preferred if the composition of the invention are used therapeutically, i.e. to treat a condition which has manifested rather than prophylactically. It may be that the composition of the invention is more effective when used therapeutically than prophylactically.

The composition of the invention can be used on any animal subject, in particular a mammal and more particularly to a human or an animal serving as a model for a disease (e.g., mouse, monkey, etc.).

In order to treat a disease an effective amount of the active composition needs to be administered to a patient. A "therapeutically effective amount" means the amount of a composition that, when administered to an animal for treating a state, disorder or condition, is sufficient to effect such treatment. The "therapeutically effective amount" will vary depending on the composition, the disease and its severity and the age, weight, physical condition and responsiveness of the subject to be treated and will be ultimately at the discretion of the attendant doctor.

It may be that to treat cancer according to the invention that the composition of the invention has to be readministered at certain intervals. Suitable dosage regimes can be prescribed by a physician.

It will be appreciated that pharmaceutical composition for use in accordance with the present invention is ideally in a form for parenteral administered, e.g. as an emulsion for injection.

Therapeutic doses will generally be between about 10 and 2000 mg/day and preferably between about 30 and 1500 mg/day. Other ranges may be used, including, for example, 50-500 mg/day, 50-300 mg/day, 100-200 mg/day.

Administration may be once a day, twice a day, or more often, and may be decreased during a maintenance phase of the disease or disorder, e.g. once every second or third day instead of every day or twice a day. The dose and the administration frequency will depend on the clinical signs, which confirm maintenance of the remission phase, with the reduction or absence of at least one or more preferably more than one clinical signs of the acute phase known to the person skilled in the art.

The invention is described further below with reference to the following non-limiting examples.

EXAMPLES

The following compounds are used in the Experiments:

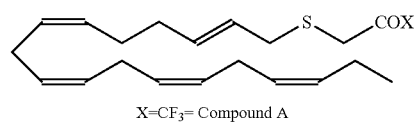

X=CF$_3$= Compound A

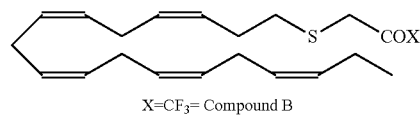

X=CF$_3$= Compound B

Example 1

Stability Studies

The formulations were prepared in duplicate for the stability study:

TABLE 1a

| Component | A/B Amount (mg/mL) | Comparative C/D Amount (mg/mL) | AY-14 Amount (mg/mL) | AY15-01 Amount (mg/mL) |
|---|---|---|---|---|
| Compound B | 5 mg | 20 mg | 2.0 mg | 2.0 mg |
| Polysorbate 80 | 5 mg | — | 2.0 mg | 2.0 mg |
| MCT Oil | 5 mg | To make 1 ml | 2.0 mg | 2.0 mg |
| Citrate buffer | To make 1 ml | — | qs to make 1 mL | a) |

The citrate buffer is composed of Citric Acid Monohydrate 1.5 mM; Trisodium Citrate dehydrate 8.5 mM and Wfl pH = 7, and argon is used for air displacement.
a) Compound B is solubilized in 10 mM sodium citrate (pH 7) by use of MCT oil 2 mg/ml and Polysorbate 80, 2 mg/ml; the samples have been saturated with argon as part of the filling process, and are filled in 10 ml freeze-stable polymer-vials.

In Table 1b below, samples have been prepared by accurately weighing out the testing material, ca 500 mg, into 10 ml volumetric flasks and dilute to volume with ACN/water 95:5. Duplicate samples are prepared for each time point.

TABLE 1b

Calculation of Compound B content in AY15-01 samples (duplicate samples).

| Samples | Weight (mg) | Dilution | Area | Compound B in sample (mg/g*) | Average Compound B (mg/g*) |
|---|---|---|---|---|---|
| AY15-01-i Start Analysis | | | | | |
| Sample 1 | 515.40 | 10 ml | 1534.2 | 1.73 | 1.72 |
| Sample 2 | 523.04 | 10 ml | 1540.4 | 1.71 | |
| AY15-01-j 2 Months Analysis | | | | | |
| Sample 1 | 505.83 | 10 ml | 1504.2 | 1.62 | 1.62 |
| Sample 2 | 509.25 | 10 ml | 1510.6 | 1.62 | |
| AY15-01-k 4 Months Analysis | | | | | |
| Sample 1 | 504.93 | 10 ml | 1481.4 | 1.60 | 1.60 |
| Sample 2 | 504.47 | 10 ml | 1486.2 | 1.61 | |
| AY15-01-l 6 Months Analysis | | | | | |
| Sample 1 | 492.74 | 10 ml | 1396.9 | 1.55 | 1.55 |
| Sample 2 | 486.07 | 10 ml | 1388.2 | 1.56 | |

*The results are reported as mg/g, thus the density of the solutions has not been taken into account.

General Procedure

Components: 2 mg Compound B/ml nano-emulsion: MCT oil 2 mg/ml and P80 2 mg/ml and Citrate buffer 10 mM

| 1. | Compound B | 791 mg |
| 2. | MCT oil | 750 mg |
| 3. | Polysorbate 80 | 750 mg |
| 4. | Sodium citrate buffer 10 mM | pH 7 to make 375 ml |

Components 1 and 2 are mixed at ambient temperature in a vessel and flushed with argon. Component 3 is added with mixing. The blend is heated to 80-85° C. in a water bath. Component 4 is added at 60-80° C. slowly with frequent mixing/vortexing. The product was sterilized by filtration, purged with argon and filled into 10 ml vials. Vials are flushed with argon before closure. Vials were frozen at −20° C.

Assay, Purity and Impurities:

The method used is a RP HPLC method using UV detection. The conditions are summarised below:

TABLE 2

| Analytical Column | 120 EC-C18 (150 × 4.6 mm, 2.7 μm particle size) |
|---|---|
| Flow | 1.5 ml/min |
| Detection wavelength | 210 nm |
| Temperature | 15° C. |
| Inj. Volume | 3 μl |
| Stop Time | 42 min |
| Post Time | 3 min |
| Mobile phase A | Water:acetonitrile:formic acid (0.02%):300:700:0.2 |
| Mobile phase B | Acetonitril:formic acid (0.02%):1000:0.2 |
| Diluent | Acetonitril/Water (95:5) |
| Gradient | Time (min)    Conc. B % |
| | 0    0 |
| | 12    80 |
| | 20    100 |

For AY-14, three months data shows no change in the parameters tested indicating good stability at −20° C.

The stability of formulations A-D and 4 repeats of AY14 is shown in the Table below

TABLE 3

| Sample | Time (months), Temperature (C.) | Sulfoxide area[1] | Thiol area[2] | Impurities[3] | Total other impurities (% area) | Comp B area (% area) |
|---|---|---|---|---|---|---|
| A | 0, rt | 3.5 | 1 | 0 | 3.8 | 91.8 |
| B | 0, rt | 3.5 | 0.8 | 0 | 3.3 | 92.4 |
| Average | | 3.5 | 0.9 | 0 | 3.55 | 92.1 |
| A | 1 mth, 5° C. | 6.1 | 0.7 | 2.1 | 3 | 88.1 |
| B | 1 mth, 5° C. | 6.3 | 0.6 | 2 | 3.1 | 88 |
| Average | | 6.2 | 0.65 | 2.05 | 3.05 | 88.05 |
| A | 1 mth, −20° C. | 3.5 | 1.2 | 0.7 | 3.4 | 91.3 |
| B | 1 mth, −20° C. | 3.5 | 1.3 | 0.6 | 3.1 | 91.6 |
| Average | | 3.5 | 1.25 | 0.65 | 3.25 | 91.45 |
| C | 0, rt | | | | | |
| D | 0, rt | | | | | |
| Average | | | | | | |
| C | 3 mth, 5° C. | 9.5 | low | 2.7 | 5.3 | 82.5 |
| D | 3 mth, 5° C. | 9.4 | low | 2.7 | 5.2 | 82.7 |
| Average | | 9.45 | low | 2.7 | 5.25 | 82.6 |
| C | 3 mth, −20° C. | 4.2 | 0.8 | 1 | 4.1 | 89.9 |
| D | 3 mth, −20° C. | 4.2 | 0.9 | 0.8 | 3.5 | 90.6 |
| Average | | 4.2 | 0.85 | 0.9 | 3.8 | 90.25 |
| C | 6 mth, 5° C. | 10.9 | low | 3.2 | 2.5 | 83.4 |
| D | 6 mth, 5° C. | 10.9 | low | 3.4 | 2.9 | 92.8 |
| Average | | 10.9 | low | 3.3 | 2.7 | 88.1 |

TABLE 3-continued

| Sample | Time (months), Temperature (C.) | Sulfoxide area[1] | Thiol area[2] | Impurities[3] | Total other impurities (% area) | Comp B area (% area) |
|---|---|---|---|---|---|---|
| C | 6 mth, −20° C. | 4.2 | 0.9 | 1.1 | 1.8 | 92 |
| D | 6 mth, −20° C. | 4.2 | 0.8 | 0.8 | 2.8 | 91.4 |
| Average | | 4.2 | 0.85 | 0.95 | 2.3 | 91.7 |
| AY14-e | 3 mth, −20° C. | 1.9 | LOQ | 0.2 | 4.2 | 93.8 |
| AY14-f | 3 mth, −20° C. | 1.8 | LOQ | 0.2 | 4.3 | 93.7 |
| AY14-g | 3 mth, −20° C. | 1.9 | 0.4 | 0.2 | 4.5 | 93.2 |
| AY14-h | 3 mth, −20° C. | 1.9 | 0.4 | 0.1 | 4.3 | 93.4 |
| AY15-01-i | 0, −20° C. Sample 1 | 1.7 | 0.2 | LOQ | 4.4 | 93.7 |
| | Sample 2 | 1.7 | 0.2 | LOQ | 4.3 | 93.8 |
| AY15-01-j | 2 mth, −20° C. Sample 1 | 2.0 | 0.2 | LOQ | 5.7 | 92.1 |
| | Sample 2 | 2.0 | 0.2 | LOQ | 6.0 | 91.8 |
| AY15-01-k | 4 mth, −20° C. Sample 1 | 2.6 | 0.3 | 0.2 | 3.8 | 93.1 |
| | Sample 2 | 2.5 | 0.4 | 0.2 | 4.5 | 92.4 |
| AY15-01-l | 6 mth, −20° C. Sample 1 | 3.0 | 0.3 | N/A | 7.6 | 89.1 |
| | Sample 2 | 3.0 | 0.4 | N/A | 6.4 | 90.2 |

LOQ low means too low to be seen.
[1]RRT 0.57 minutes,
[2]RRT 1.41 minutes,
[3]RRT 3.78 minutes.
The experiments for AY15-01 samples were performed in duplicate, as can be seen from the sets of data for sample 1 and sample 2.
It should be noted that the chromatograms are manually integrated and some inaccuracy is inherent in the integration due to overlapping/tailing peaks and "ghost peaks". However, the amount of sulfoxide reported should be considered accurate, as no ghost peaks/overlapping peaks are observed in this retention area.
As can be seen for the above data, the Compound B peak area for formulations A/B were essentially unchanged even after 6 months of storage at −20° C.

Example 2

Further formulations have been prepared:

TABLE 4

AY12 Micelles

| Ingredient | AY12-01 | AY12-02 | AY12-03 |
|---|---|---|---|
| Compound B (100%) | 1.0 mg | 2.0 mg | 5.0 mg |
| Polysorbate 80 | 5.0 mg | 10.0 mg | 25.0 mg |
| MCT Oil | 5.0 mg | 10.0 mg | 25.0 mg |
| EDTA | 5 mM | 5 mM | 5 mM |
| Water for Injection | qs to make 1 mL | qs to make 1 mL | qs to make 1 mL |

All three formulations are at pH=7, and argon is used for air displacement. These examples can be summarised as:

AY12-01: Compound B 1.0 mg/ml IV inj ("Micelles": P80 5 mg/ml MCT oil 5 mg/ml Na-EDTA 5 mM pH 7)

AY12-02: Compound B 2.0 mg/ml SC inj. ("Micelles": P80 10 mg/ml MCT oil 10 mg/ml Na-EDTA 5 mM pH 7)

AY12-03: Compound B 5.0 mg/ml SC inj. ("Micelles": P80 25 mg/ml MCT oil 25 mg/ml Na-EDTA 5 mM pH 7)

These materials are tested against comparative examples:

AY12-04: Compound B 2.0 mg/ml SC inj. (in pure MCT oil)

AY12-05: Compound B 5.0 mg/ml SC inj. (in pure MCT oil)

AY12-06: Compound B 2.5 mg/ml IP inj. (in pure DMSO)

The data is reported in table 5

| Sample | Time (months), Temperature (C.) | Sulfoxide area[1] | Thiol area[2] | Impurities[3] | Total other impurities | Comp B area |
|---|---|---|---|---|---|---|
| AY12-01 | 0 | 0.7 | Not detected | LOQ | 2.1 | 97.2 |
| AY12-01 | 0 | 0.8 | Not detected | LOQ | 2.4 | 96.8 |
| AY12-02 | 0 | 0.7 | Not detected | LOQ | 2.5 | 96.9 |
| AY12-02 | 0 | 0.7 | Not detected | LOQ | 2.8 | 96.5 |
| AY12-03 | 0 | 0.7 | Not detected | LOQ | 2.9 | 96.4 |
| AY12-03 | 0 | 0.7 | Not detected | LOQ | 2.5 | 96.8 |
| AY12-04 | 0 | 3.6 | Not detected | LOQ | 2.7 | 93.8 |
| AY12-04 | 0 | 3.6 | Not detected | LOQ | 2.7 | 93.7 |
| AY12-05 | 0 | 4.3 | Not detected | LOQ | 2.4 | 93.4 |
| AY12-05 | 0 | 4.2 | Not detected | LOQ | 2.3 | 93.5 |
| AY12-06 | 0 | 0.8 | Not detected | LOQ | 3.1 | 96.1 |
| AY12-06 | 0 | 0.8 | Not detected | LOQ | 2.6 | 96.6 |
| AY12-01 | 1 mth, 2-8° C. | 1.7 | Not detected | 0.3 | 3.2 | 94.8 |
| AY12-01 | 1 mth, 2-8° C. | 1.7 | Not detected | 0.3 | 3.5 | 94.5 |
| AY12-02 | 1 mth, 2-8° C. | 1.1 | 0.1 | 0.2 | 3.8 | 94.8 |
| AY12-02 | 1 mth, 2-8° C. | 1.1 | 0.2 | 0.2 | 3.3 | 95.2 |
| AY12-03 | 1 mth, 2-8° C. | 1.3 | 0.1 | 0.2 | 3.7 | 94.6 |
| AY12-03 | 1 mth, 2-8° C. | 1.3 | 0.1 | 0.2 | 3.7 | 94.7 |
| AY12-04 | 1 mth, 2-8° C. | 5.9 | 0.2 | LOQ | 3.6 | 90.3 |
| AY12-04 | 1 mth, 2-8° C. | 5.9 | 0.3 | LOQ | 3.8 | 90.1 |
| AY12-05 | 1 mth, 2-8° C. | 6.8 | 0.3 | LOQ | 4.4 | 88.6 |

| Sample | Time (months), Temperature (C.) | Sulfoxide area[1] | Thiol area[2] | Impurities[3] | Total other impurities | Comp B area |
|---|---|---|---|---|---|---|
| AY12-05 | 1 mth, 2-8° C. | 6.8 | 0.3 | LOQ | 4.2 | 88.7 |
| AY12-06 | 1 mth, 2-8° C. | 3.2 | 0.5 | LOQ | 5.3 | 91.1 |
| AY12-06 | 1 mth, 2-8° C. | 3.2 | 0.4 | LOQ | 5.2 | 91.2 |

Example 3

Background

Collagen induced arthritis (CIA) is a commonly used arthritis model in preclinical research. In this model, the disease is induced by injecting type II collagen (a cartilage component) emulsified in complete Freund's adjuvant in the high responder DBA/1 mouse strain (or in other species such as the rat or the monkey). Introduction of collagen breaks tolerance and directs an immune-mediated inflammatory attack on the joints that can be measured by evaluating standard disease parameters as based on an arthritis index score: (Animal models for arthritis: innovative tools for prevention and treatment, Ann Rheum Dis. 2011 August; 70 (8): 1357-62).

Test Article & Formulation

The following compound is used:

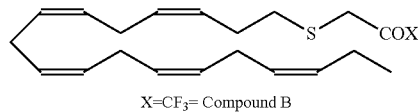

X=CF$_3$= Compound B

Compound B was formulated for subcutaneous administration in a nano-emulsion containing 2 mg/ml Compound B, 2 mg/ml MCT oil (Lipoid), 2 mg/ml Polysorbate 80 (Fluka) and sodium citrate buffer 10 mM (pH 7). The final solution was sterilized by filtration and saturated with Argon 5.0 AGA prior to aliquoting in 10 ml tubes stored at −20° C. till further use.

Animals 7-10 weeks old male DBA/1 mice were sourced from Beijing Vital River laboratories, China (average weight at the beginning of the study: 18-25 g). The animals were housed in an animal room set at a temperature of 23±2° C., humidity of 40-70%, under a 12-hour light/12-hour dark cycle. SPF (Serum Pathogen Free) mouse growth breeding feed (Beijing KeaoXieli feed Co. LTD) was provided ad libitum throughout the in-life portion of the study. Water was available ad libitum.

Collagen Induced Arthritis (CIA)—Experimental Design

Groups 40 male DBA/1 mice were divided into 4 groups and treated according to the design below.

Induction of CIA

CIA was induced in male DBA/1 mice (except sham group) by immunization with 0.1 ml emulsion containing an equal volume of bovine type II collagen solution (2 mg/me and Freund's complete adjuvant (FCA) at the tail base. The first injection was given on Day 0 and the second injection as booster was given on Day 21. Treatment started one hour before the second collagen injection and continued for at least 21 days.

CIA Assessment and Treatment

CIA was assessed in mice by two blinded observers to measure paw swelling with a capacity measurement method. The occurrence of arthritis was observed by scoring all four paws for severity of erythema and swelling, using a clinical score ranging from 0 (no swelling) to 4 (severe swelling and erythema) as below, yielding a maximum Arthritis Index (AI) score of 16 (4 paws×max score per paw): J Med Chem. 2014 Sep. 25; 57 (18):7523-35, Kokotos et al.

Score Grading:

| Grade | Degree |
|---|---|
| 0 | No swelling, normal appearance |
| 1 | Slight swelling and erythema of the ankle, wrist or digits |
| 2 | Moderate swelling and erythema of the ankle, wrist or digits |
| 3 | Severe swelling and erythema of the ankle, wrist or digits |
| 4 | Maximal inflammation with joint rigidity; very severe |

The detailed dosing info per treatment group was as follows.

Group 1: 7 mice that have received no collagen, treated with vehicle DMSO (everyday) for 3 weeks.

Group 2: 11 mice were induced by collagen and treated with vehicle DMSO (everyday) for 3 weeks.

Group 3: 11 mice were induced by collagen and treated with Compound B (5 mg/kg, Daily) for 3 weeks.

Group 4: 11 mice were induced by collagen and treated with Compound B (10 mg/kg, Daily) for 3 weeks.

At the end of the study, all mice were euthanized according to applicable ethical laws by carbon dioxide inhalation.

Clinical Observations

The physical condition of the animals and clinical signs (if any) were recorded for individual animals, once before commencement of treatment and once daily during the study. Observation was performed at the same time interval each day. Body weigh measurements were also conducted on the day of allocation to its corresponding group and then on each day of arthritis evaluation.

TABLE 6

| Group | Treatment | Dosing route | Dosing schedule | Dosing volume | Animals number |
|---|---|---|---|---|---|
| 1 | Sham (Non-treatment) | — | Daily | 2 ml/kg | 7 |
| 2 | Vehicle (DMSO) | Intraperitoneal | Daily | 2 ml/kg | 11 |
| 3 | Compound B 5 mg/kg | Subcutaneous | Daily | 2.5 ml/kg | 11 |
| 4 | Compound B 10 mg/kg | Subcutaneous | Daily | 5 ml/kg | 11 |

Statistical Analysis

Data was given as Mean±SD. The statistical analysis of the results were performed by the Independent-Sample t test. Values for p<0.05 were considered significant.

Results

Effect of Compound B on Body Weight in the CIA Mouse Model

From Day 32 to the end of the experiment a significant reduction in body weight was observed in the CIA control mice, compared with the sham mice (p<0.005). Such weight loss or wasting is typical of this model as CIA progresses. There was a significant inhibition of the body weight loss of Compound B 5 mg/kg group on Day 34 and 39~43 (p<0.05~0.005) and Compound B 10 mg/kg group on Day 25 and 32~43 (p<0.05~0.005), compared with vehicle treated CIA group (Table 7).

Effect of Compound B on Arthritis Index (AI) in the CIA Mouse Model

A 100% incidence of CIA was observed by day 32 in CII-immunized mice, with a maximum AI of 4.18 observed at Day 43 post immunization. The AI and incidence of all groups increased in a time-dependent mode from day 27 to day 43.

The AI of Compound B 10 mg/kg group on Day 41~43 was significantly reduced (p<0.05) in comparison to the CIA control group. The AI index of Compound B 5 mg/kg group was also reduced when compared with that of the CIA control group, however, the reduction reached no statistical significance (p>0.05) (Table 8).

No other clinical observations or side effects were evident in animals treated with Compound B.

The study results indicated, among other things, that arthritis was successfully induced in DBA/1 mice. Treatment with subcutaneously administered. Compound B reduced arthritis symptoms and disease score in the absence of side effects.

TABLE 7

Compound B on body weight in the CIA mouse model

| Group | Dose (mg/kg) | Day -1 | 20 | 25 | 27 | 29 | 32 | 34 | 36 | 39 | 41 | 43 |
|---|---|---|---|---|---|---|---|---|---|---|---|---|
| Sham | — | 21.57 ± 1.93 | 23.17 ± 2.01 | 21.8 ± 2.17 | 21.59 ± 2.15 | 22.14 ± 2.28 | 22.4 ± 2.1 *** | 22.4 ± 2.04 *** | 22.66 ± 2.14 *** | 22.34 ± 2.11 *** | 22.04 ± 1.91 *** | 22.41 ± 2.03 *** |
| Vehicle | — | 21.62 ± 1.06 | 22.16 ± 1.14 | 20.48 ± 1.19 | 20.6 ± 1.28 | 20.55 ± 1.67 | 19.36 ± 1.48 | 19.17 ± 1.41 | 19.52 ± 1.33 | 19.16 ± 1.23 | 19.27 ± 1.36 | 19.46 ± 1.4 |
| Cpd B | 5 | 21.55 ± 1.19 | 22.5 ± 1.27 | 21.53 ± 1.18 | 21.06 ± 1.37 | 20.85 ± 1.28 | 20.25 ± 1.41 | 20.55 ± 1.25 * | 20.63 ± 1.27 | 20.59 ± 1.15 * | 21.09 ± 1.24 *** | 21.39 ± 1.01 *** |
| Cpd B | 10 | 22.12 ± 1.37 | 22.3 ± 1.44 | 21.69 ± 1.4 * | 21.37 ± 1.5 | 21.61 ± 1.75 | 21.38 ± 2.04 * | 21.46 ± 2.1 ** | 21.81 ± 2.25 ** | 21.7 ± 1.9 *** | 21.95 ± 1.76 *** | 22.35 ± 1.59 *** |

* p < 0.05,  p < 0.01, * p < 0.005 vs CIA control group

TABLE 8

Effect of Compound B on arthritis index (AI) in the CIA mouse model

| Group | Dose (mg/kg) | Day -1 | 20 | 25 | 27 | 29 | 32 | 34 | 36 | 39 | 41 | 43 |
|---|---|---|---|---|---|---|---|---|---|---|---|---|
| Sham | — | 0 ± 0 | 0 ± 0 | 0 ± 0 | 0 ± 0 | 0 ± 0 * | 0 ± 0 *** | 0 ± 0 *** | 0 ± 0 *** | 0 ± 0 *** | 0 ± 0 *** | 0 ± 0 *** |
| Vehicle | — | 0 ± 0 | 0 ± 0 | 0 ± 0 | 0.36 ± 0.67 | 1 ± 1 | 2.73 ± 1.49 | 3.82 ± 1.66 | 4 ± 1.9 | 4.09 ± 1.81 | 4.09 ± 1.81 | 4.18 ± 1.94 |
| Cpd B | 5 | 0 ± 0 | 0 ± 0 | 0 ± 0 | 0.36 ± 0.67 | 1.27 ± 1.19 | 3 ± 1.79 | 3.27 ± 2.33 | 3.36 ± 2.42 | 3.36 ± 2.58 | 3 ± 2.49 | 2.91 ± 2.34 |
| Cpd B | 10 | 0 ± 0 | 0 ± 0 | 0 ± 0 | 0.18 ± 0.6 | 0.55 ± 1.51 | 1.36 ± 1.86 | 2 ± 2.97 | 2.18 ± 2.96 | 2.27 ± 2.9 | 2.09 ± 2.55 * | 2.09 ± 2.30 * |

* p < 0.05 p < 0.01, * p < 0.005 vs CIA control group

Example 4

The following compound is used:

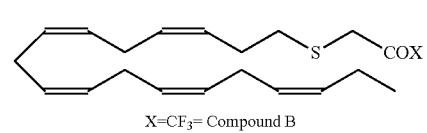

X=CF₃= Compound B

The STZ diabetic nephropathy model is frequently used in preclinical diabetic & kidney research as it recapitulates several features of the human disease. In this model, streptozotocin (STZ), a glucosemoiety with a very reactive nitrosourea group from the mould Streptomyces griseus, is injected in rats (or mice) to induce selective destruction of the insulin-producing β-cells of the pancreas. This results in increasing blood glucose levels which within a period of 4 to 6 weeks (and extending up to 24 weeks) lead to progressive kidney disease characterized by altered renal haemodynamics, increased glomerular basement membrane thickness and promotion of the development of inflammation and fibrosis in the kidney. Importantly, disease progression in this model can be monitored by analysing increasing levels of various biochemical (urine protein, albumin, protein to creatinine rations etc) or histological markers (a-SMA, Fibronectin etc) allowing direct assessment of action of chronically administered agents, Tesch, Nephrology (Carlton). 2007 June; 12 (3):261-6.

Test Article & Formulations

Compound B was formulated for subcutaneous administration in a nano-emulsion containing 2 mg/ml Compound B, 2 mg/ml MCT oil (Lipoid), 2 mg/ml Polysorbate 80 (Fluka) and sodium citrate buffer 10 mM (pH 7). The final solution was sterilized by filtration and saturated with Argon 5.0 AGA prior to aliquoting in 10 ml tubes stored at −20° C. till further use. A separate Polysorbate 80- and sodium citrate buffer-based vehicle solution without Compound B and MCT oil was also prepared, sterilized, aliquoted and stored, serving as the subcutaneous vehicle control used in the STZ animal study.

Animals 5-6 weeks old male Sprague-Dawley (SD) rats were sourced from Harlan Laboratories, Houston, Tex., USA (average weight at the beginning of the study: 125-135 g). The animals were housed in an animal room set at a temperature of 23±2° C., humidity of 40-70%, under a 12-hour light/12-hour dark cycle. Labdiet 5001 (PMI Nutrition International) was provided ad libitum throughout the in-life portion of the study. Water was available ad libitum.

Experimental Instruments and Assays

The following instruments were used:

Chemistries:

Blood glucose: ReliOn Ultima Glucometer & test strips

Urine protein: Bradford assay kit: Quick Start© Bradford dye reagent and BSA standard set. Catalog #500-0205 (Bio-Rad Laboratories, Inc. Hercules, Calif., USA). Quick Start is a colorimetric assay based on the reaction of proteins with an alkaline copper tartrate solution and Folin reagent.

Urine Albumin: Nephrat II Quantitative Determination of Rat Urinary Albumin Kit. Catalog #NR002 Strip Plate (Exocell Inc., Philadelphia, Pa., USA). Nephrat II is a direct competitive ELISA for the quantitative determination of urinary albumin in rat specimens. An anti-rat albumin antibody-HRP conjugate is allowed to react with standards and diluted urine samples. A chromogenic substrate, TMB, is added to the wells, and color development ensues. Color intensity is inversely proportional to the log of rat albumin concentration of the sample.

Urine creatinine: The Creatinine Companion Assay Kit. Catalog #1012 (Exocell, Inc., Philadelphia, Pa., USA) was used to measure urine creatinine. The procedure is an adaptation of the alkaline picrate method and entails determination of the differential absorbance in a sample before and after the additions of acid to correct for color generation due to interfering substances.

Assay instrument: Bio-Rad iMark microplate reader.

Immunohistochemistry:

ImmPRESS HRP Anti-Mouse IgG, Rat adsorbed (Peroxidase) Polymer Detection Kit, MP-7422, Vector Laboratories, Inc. Burlingame, Calif.

Quenching Endogenous Peroxidase Activity: 0.3% $H_2O_2$

Peroxidase (HRP) Substrate Kit, 3,3'-diaminobenzidine Kit, SK-4100

Histopathological analysis was conducted using an Olympus BX51 research microscope equipped with a DP-71 digital camera. Image-Pro Plus software was used for computer-assisted image analysis.

Groups 50 male Sprague-Dawley SD rats were divided into 5 groups of 10 rats and treated according to the design below.

TABLE 9

Groups and Treatments

| Group | Description | Dosing route | Dosing volume | Animals No. |
| --- | --- | --- | --- | --- |
| 1 | Sham (vehicle) | sc, daily | 0.67-1.0 ml | 10 |
| 2 | STZ control (vehicle) | sc, daily | 0.67-1.0 ml | 10 |
| 3 | STZ + Compound B [2 mg/kg] | sc, daily | 0.67-1.0 ml | 10 |
| 4 | STZ + Compound B [4 mg/kg] | sc, daily | 0.67-1.0 ml | 10 |
| 5 | STZ + Compound B [6 mg/kg] | sc, daily | 0.67-1.0 ml | 10 |

Induction of Diabetic Nephropathy (DN)

DN was induced in rats (except sham group—Group 1) by tail vein injection of streptozotocin (STZ) (S0130, Sigma Aldrich Corporation, St. Louis, Mo. USA) at a dose of 50 mg/kg in 0.4-0.45 ml of citrate buffer. Sham control received a similar injection in citrate buffer in the absence of STZ. The injection was given on Day 0. Treatment started on Day 3 and continued for up to 6 weeks.

Group Treatments

Table 9 above summarizes the treatment schedules of the study. Overall, 3 different doses (2, 4 and 6 mg/kg) of Compound B were administered subcutaneously (SC) for 6 weeks following induction of diabetes. Vehicle control was administered in Group 1 (animals that did not receive STZ) and Group 2 (animals that have received STZ), daily for 6 weeks. Periodical collection of urine and blood was performed to allow multiple biochemical analyses as described below.

Group Assessments

The following assessments were performed on animals of all groups throughout the course of this study:

Clinical signs: All clinical signs were recorded for individual animals, once before commencement of treatment and once daily during the study. Observation was performed at the same time interval each day.

Body weight: Each animal was weighed on the day of allocation to its corresponding group and then every time prior to injection of each test article for dose volume adjustments.

Sample Collection & Assessments

Clinical Chemistry Assessments

Blood Glucose: Blood glucose was measured at the 0, 1, 2, 4, and 6 week time points by collecting a drop of blood from freshly pierced tip of the tail using a sterile 25 G needle. Blood glucose measurements were conducted immediately by direct test strip analysis.

Urine Protein: At the 0, 2, 3, 4, 5 and 6 week time points the rats were set up in metabolic cages for urine collection. Measurements of urine protein were performed on 12 hour void volumes ranging from 7-16 ml. All 12 hour urine protein values (expressed in mg) were extrapolated to 24 hours to correspond to standard practice in the field.

Urine Albumin: Measurements of urine albumin were performed on samples collected at the 0 and 6 week time points. As with urine protein data the albumin values were extrapolated to 24 hours to correspond to standard practice in the field.

Urine Creatinine: Measurements of urine creatinine were performed on samples collected at the 0 and 6 week time points. The urine creatinine data was used to determine protein and albumin ratios and expressed as milligram Creatinine: gram protein or albumin (mg/g) to correspond to standard practice in the field.

Terminal Studies

Euthanasia: Animals that have completed the scheduled test period were disposed with carbon dioxide according to standard ethical guidelines. All animals were subjected to necropsy, supervised by a pathologist, as detailed below. The scores of sacrificed animals were included in the calculations of the mean group scores throughout the experiment and until its end.

Necropsy: On the completion day, sacrifices were performed at approximately 5 hours after the last application. A macroscopic examination of the animal was performed on all sacrificed animals and any abnormality was recorded.

Kidney tissue collection: Immediately after the blood collection, the left and right kidneys were excised, cut in 3-4 mm thick coronal slices. A central slice of kidney was placed in formalin for subsequent embedment and routine histological assessments. Several slices were placed on aluminum foil strips and flash frozen by immersion in liquid nitrogen and placed in air-tight storage vials for subsequent immunohistochemical assessment. All samples were frozen at −80° C. until analyzed. The following analyses were performed:

Histopathological Analysis

Glomerular α-SMA staining (for area of glomerular mesangial activation): Frozen kidney sections were cut and batch stained for α-SMA using a monoclonal primary antibody (Clone 1A4, Sigma Chemical Co, St Louis, Mo.) using standard immunohistochemical methods. Peroxidase-conjugated second antibody was detected utilizing ImmPress polymer detection reagents according to the manufacturer's instructions (Vector Laboratories, Inc. Burlingame, Calif.). Group 3 (STZ+Compound B [2 mg/kg] sc) was omitted from the analysis.

Glomerular fibronectin staining (for area of glomerular matrix): Frozen kidney sections were cut and batch stained for fibronectin staining using a monoclonal primary antibody (Clone IST-9) AbCam (Cambridge, Mass.) and standard immunohistochemical methods conducted at Probetex (See attached SOP). Group 3 (STZ+Compound B [2 mg/kg] sc) was omitted from the analysis.

Computer Assisted Image Analysis

α-SMA and Fibronectin Staining

α-SMA: (area of mesangial cell activation): Glomerular α-SMA staining was assessed by image analysis. Digital images were taken of twenty-five random glomeruli at an objective magnification of 10×. Total area of glomerular staining was measured by computer assisted image analysis using the tracing tool of Image-Pro imaging software to capture glomerular area. The images were segmented and converted to gray scale then pseudo-colored representing background (blue) and positive staining (red) areas and percent area representing α-SMA positive mesangial cells was quantitated. Data were saved on an excel spreadsheets and average staining area was calculated and analyzed statistically.

Fibronectin: (area of mesangial cell matrix accumulation): Image analysis of glomerular staining for fibronectin was conducted using the same methods discussed above for α-SMA.

Results—Clinical

Blood glucose: Average blood glucose at start of the study was 127 mg/dl (range 120-131 mg/dl). All rats receiving STZ became diabetic (blood glucose >200 mg/dl) at the start of the experiment, except for rats #11 (Group 2), 21, 31 and 32 (Group 4), and 41 (Group 5). Of these rats, only #11 progressed to values greater than 200 mg/dl for the remainder of the study. Most remaining rats developed hyperglycemia by the 2 week time point. However, despite elevated glucose readings at the start of the 2 week period, some of the rats (distributed among the groups) did not sustain their diabetic status. All remaining animals at 4 and 6 weeks had glucose values above 200 mg/dl. The sensitivity of the meter measures a maximum of 500 mg/dl, thus some of these values may be under estimates. Average blood glucose levels for each group are illustrated in the summary table below.

TABLE 10

Blood Glucose Measurements

| Group | 0 wk | 3 days | 6 days | 2 wks | 4 wks | 6 wks |
|---|---|---|---|---|---|---|
| G1: Critrate (iv) + Vehicle, (sc, daily) | 129.8 | 111.6 | 111.8 | 122.0 | 112.7 | 110.3 |
| G2: STZ (iv) + Vehicle, (sc, daily) | 130.0 | 288.6 | 362.7 | 359.6 | 311.8 | 293.0 |
| G3: STZ + Compound B [2 mg/kg] sc, daily | 129.6 | 300.3 | 339.5 | 340.1 | 239.5 | 210.8 |
| G4: STZ + Compound B [4 mg/kg] sc, daily | 120.3 | 285.5 | 349.8 | 327.4 | 272.0 | 251.0 |
| G5: STZ + Compound B [6 mg/kg] sc, daily | 129.0 | 305.1 | 372.8 | 370.1 | 321.8 | 304.3 |

Urine Protein: Average pretrial urine protein values ranged from 0.7 to 3.7 mg/dl among the groups. STZ controls (Group 2), showed an initial spike in proteinuria at 2 weeks with 43.5 mg/24 hrs. These values lessened thereafter, but remained elevated at 27.2, 33.9, 30.2 and 34.2 mg/24 hours at 3, 4, 5, and 6 weeks, respectively. Proteinuria in vehicle controls (Group 1) ranged from 17.0-24.6 mg/24 hours throughout the course of the study. Compound B treatment resulted in a reduction in proteinuria relative to STZ+vehicle as indicated in Table 11 below.

Urine protein-to-creatinine ratios provide more accurate estimates of the urinary protein excretion rate and are not affected by hydration. Thus, urine protein to urine creatinine ratios were determined at 0 and 6 week time points. The results showed similar trends as protein measurements alone, however differences among the groups were more defined. For example, STZ+vehicle showed a 70% increase in UP/CR (1715: 2919) relative to citrate control at the 6 week time point. All treatment groups (except low-dose Compound B) had ratios less than STZ+vehicle; reductions followed a dose-dependent pattern.

TABLE 11

Proteinuria & Protein/Creatinine Ratio (0 time to 6 weeks).

| Group | Proteinuria (mg/24 hr) | | | | | | UP/CR mg/g | |
|---|---|---|---|---|---|---|---|---|
| | 0 wk | 2 wks | 3 wks | 4 wks | 5 wks | 6 wks | 0 wk | 6 wks |
| G1: Critrate (iv) + Vehicle, (sc, daily) | 0.8 | 24.6 | 17.0 | 20.8 | 20.5 | 21.9 | 140.5 | 1714.9 |
| G2: STZ (iv) + Vehicle, (sc, daily) | 2.7 | 43.5 | 27.2 | 33.9 | 30.2 | 34.2 | 497.9 | 2918.7 |
| G3: STZ + Compound B [2 mg/kg] sc, daily | 1.5 | 30.8 | 30.4 | 39.4 | 39.1 | 40.0 | 239.6 | 3159.0 |
| G4: STZ + Compound B [4 mg/kg] sc, daily | 1.1 | 18.8 | 19.0 | 24.5 | 25.5 | 27.7 | 165.5 | 2384.5 |
| G5: STZ + Compound B [6 mg/kg] sc, daily | 3.7 | 21.4 | 21.7 | 22.5 | 27.1 | 25.8 | 650.0 | 1903.7 |

Urine Albumin: Urine albuminuria is a more sensitive measurement of glomerular permeability defects than urine protein, particularly in diabetic nephropathy. As with urine protein-to-creatinine, albumin-to-creatinine ratios provide more accurate estimates of the urinary albumin excretion rate, and are not affected by hydration. Thus, urine albumin and urine albumin:creatinine ratios were measured at 0 and 6 week time points. The results showed similar trends observed for urine protein data where baseline average pretrial urine albumin:creatinine ratios ranged from 128 to 387 among the groups. Albumin:creatinine ratio in citrate controls (Group 1) averaged 457 at 6 weeks of diabetes. The highest albumin:creatinine ratio was observed in the STZ+vehicle (Group 2) which increased to 1584 at 6 weeks of diabetes. All groups of rats treated with STZ+Compound B had albumin:creatinine ratios less than STZ+vehicle (Table 12).

TABLE 12

Urine Albumin & Urine Albumin/Creatinine Ratio.
Urine Albumin & UA/Creatine Ratio

| Group | mg/24 hr | | UA/CR mg/g | |
|---|---|---|---|---|
| | 0 wk | 6 wks | 0 wk | 6 wks |
| G1: Critrate (iv) + Vehicle, (sc, daily) | 1.3 | 5.6 | 247.2 | 456.6 |
| G2: STZ (iv) + Vehicle, (sc, daily) | 2.3 | 18.5 | 386.7 | 1583.6 |
| G3: STZ + Compound B [2 mg/kg] sc, daily | 0.8 | 18.8 | 128.5 | 1492.4 |
| G4: STZ + Compound B [4 mg/kg] sc, daily | 0.8 | 10.9 | 127.8 | 942.9 |
| G5: STZ + Compound B [6 mg/kg] sc, daily | 1.7 | 13.9 | 302.3 | 1011.9 |

Body Weights, Toxicity of Compounds, and Mortality

Sham-vehicle (Group 1) rats progressively gained weight as expected. Growth of all animals treated with STZ was stunted relative to sham based on average body weight measurements for each group. The health of the animals throughout the course of the study appeared very good and there were no toxicities or mortality observed for Compound B treated groups.

Results—Histopathology

Glomerular α-SMA Staining (Mesangial Cell Activation)

Basal glomerular mesangial cell a-SMA staining is enhanced upon activation in a number of renal diseases including diabetic nephropathy Sham controls (Group 1) had the least mesangial a-SMA where average areas of staining were 2.1% of the glomerular area. Vehicle-treated STZ controls (Group 2) showed the highest level of mesangial α-SMA staining reaching 4.6% of the glomerular area. Treatment with Compound B blunted STZ related mesangial cell activation and a-SMA staining in all treatment groups was less than STZ-vehicle controls (Table 13).

TABLE 13

Glomerular α-SMA staining (percentage of staining per field)

| a-SMA staining | Group 1 | Group 2 | Group 4 | Group 5 |
|---|---|---|---|---|
| Mean | 2.10 | 4.63 | 3.57 | 3.21 |
| SD | 0.95 | 1.76 | 1.21 | 1.16 |

Glomerular Fibronectin Staining (Mesangial Matrix Expansion)

Glomerular fibronectin staining, used as an index of matrix accumulation, showed similar trends as observed for a-SMA. As with a-SMA, glomerular mesangial Fn staining is enhanced upon activation in renal disease including diabetic nephropathy. Basal Fn expression in sham controls (Group 1) averaged 18.2% of the glomerular area. Vehicle-treated STZ controls (Group 2) showed high levels of mesangial Fn staining reaching 22.8% of the glomerular area. Treatment with Compound B resulted in a significant reduction in Fn expression relative to vehicle controls (Table 14).

TABLE 14

Glomerular FN staining (percentage of staining per field)

| FN staining | Group 1 | Group 2 | Group 4 | Group 5 |
|---|---|---|---|---|
| Mean | 18.2 | 22.8 | 13.1 | 15.3 |
| SD | 2.9 | 4.3 | 4.5 | 3.1 |

Streptozotocin (STZ) induced diabetes and diabetic nephropathy typical of this model as indicated by increased blood glucose, proteinuria, albuminuria, and histopathological changes characterized by glomerular mesangial cell activation (assessed by acquisition of alpha-smooth muscle actin, α-SMA) and accumulation of matrix protein (fibronectin) relative to sham controls. Compound B, administered in a subcutaneous formulation, was effective in reducing proteinuria, albuminuria, urine protein:creatinine and urine albumin:creatinine ratios in this model (especially at the high dose). Similarly, Compound B reduced glomerular expression of glomerular α-SMA and Fn-protein expression assessed by immunohistochemical evaluation. Overall, Compound B did not induce side effects during a 6-week course of treatment.

The invention claimed is:

1. A composition in the form of an aqueous emulsion comprising:
   (i) 1 to 20 mg/ml of a compound of the following formula:

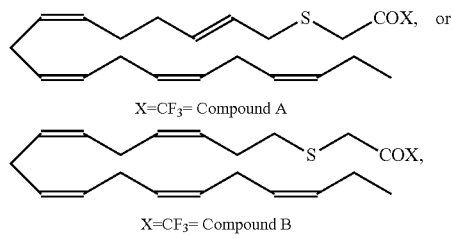

or a salt thereof;
   (ii) 1 to 20 mg/ml of a polysorbate surfactant;
   (iii) 1 to 20 mg/ml of a triglyceride; and
   (iv) a buffer.

2. The composition of claim 1, comprising Polysorbate 80.

3. The composition of claim 1, comprising MCT oil.

4. The composition of claim 1, wherein the buffer is citrate buffer.

5. The composition of claim 1, wherein the composition is isotonic.

6. The composition of claim 1, wherein the composition has a pH of about 6.0-9.0.

7. The composition of claim 1, comprising
   (i) 1 to 10 mg/ml of compound A or B;
   (ii) 1 to 10 mg/ml of a polysorbate surfactant; and
   (iii) 1 to 10 mg/ml of a triglyceride.

8. The composition of claim 1, further comprising a chelating agent, an antioxidant or both.

9. An article of manufacture comprising a container holding the composition of claim 1 and optionally, directions for using the composition.

10. The article of manufacture of claim 9, further comprising an inert gas for displacing air.

11. The composition of claim 1 in the form of an emulsion comprising
   about 2 mg of compound B;
   about 2 mg of Polysorbate 80;
   about 2 mg of MCT oil; and
   about 10 mmol of citrate buffer.

12. An article of manufacture comprising a container holding the composition of claim 11 and optionally, directions for using the formulation.

13. The composition of claim 1 in the form of an emulsion comprising:
   from about 1 mg to about 500 mg of compound A or B

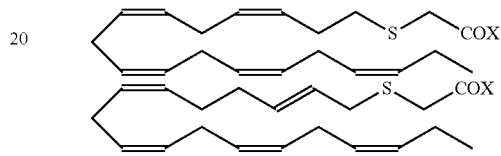

or a salt thereof;
   from about 0.1 mg to about 10 mg of Polysorbate 80;
   from about 0.1 mg to about 10 mg of MCT oil; and
   a buffering agent.

14. A method of treating or preventing an inflammatory or proliferative condition comprising administering to a mammal, in need thereof, an effective amount of a composition as defined in claim 1.

15. The method of claim 14, comprising parenteral administration of the composition.

16. The method of claim 14, comprising i.v., i.m., or s.c. administration of the composition.

* * * * *